United States Patent
Hundley et al.

(10) Patent No.: US 6,465,460 B1
(45) Date of Patent: Oct. 15, 2002

(54) COMPOSITIONS AND METHODS FOR PREVENTION AND TREATMENT OF PROTOZOAL DISEASE

(75) Inventors: Bruce Hundley, Versailles, KY (US); Robert Maclin, Lexington, KY (US)

(73) Assignee: New Ace Research Company, Versailles, KY (US)

( * ) Notice: Subject to any disclaimer, the term of this patent is extended or adjusted under 35 U.S.C. 154(b) by 0 days.

(21) Appl. No.: 09/806,975

(22) Filed: Sep. 13, 2001

Related U.S. Application Data

(60) Provisional application No. 60/103,543, filed on Oct. 8, 1998, and provisional application No. 60/112,175, filed on Dec. 14, 1998.

(51) Int. Cl.[7] .................. A61K 31/53; A01N 43/66
(52) U.S. Cl. .................. 514/242; 514/241; 514/275
(58) Field of Search ............... 514/242, 241, 514/275

(56) References Cited

U.S. PATENT DOCUMENTS

| | | | | |
|---|---|---|---|---|
| 4,219,552 A | | 8/1980 | Haberkorn et al. | |
| 4,296,104 A | | 10/1981 | Herschler | |
| 4,837,216 A | | 6/1989 | Melhorn et al. | |
| 4,913,901 A | | 4/1990 | Schlager | |
| 4,933,341 A | | 6/1990 | Lindner et al. | |
| 4,935,423 A | | 6/1990 | Lindner et al. | |
| 4,952,570 A | * | 8/1990 | Boeckx et al. | 514/242 |
| 4,968,795 A | | 11/1990 | Lindner et al. | |
| 5,114,938 A | | 5/1992 | Lindner et al. | |
| 5,141,938 A | | 8/1992 | Lindner et al. | |
| 5,188,832 A | | 2/1993 | Melhorn et al. | |
| 5,196,562 A | | 3/1993 | Lindner et al. | |
| 5,214,043 A | | 5/1993 | Lindner et al. | |
| 5,256,631 A | | 10/1993 | Lindner et al. | |
| 5,464,837 A | | 11/1995 | Melhorn et al. | |
| 5,830,893 A | | 11/1998 | Russell | |
| 5,883,095 A | * | 3/1999 | Granstrom et al. | 514/241 |
| 6,004,585 A | | 12/1999 | Grofmeyer et al. | |
| 6,034,116 A | | 3/2000 | Assmann et al. | |
| 6,150,361 A | | 11/2000 | Kennedy | |
| 6,194,408 B1 | | 2/2001 | Kennedy | |

FOREIGN PATENT DOCUMENTS

WO 00/37084 12/1998

OTHER PUBLICATIONS

Goodman & Gilman's The Pharmacological Basis of Therapeutics, 1990, Chapters 47 and 52, Pergamon Press.
Egorin et al., Clin. Pharm & Therap., 7/82, 32(1):123–128.
Rubinstein et al., Experimentia, 1980, 36:92–93.
U.S. Dept. HHS, FDA, FDA, Cntr. Vet. Med. Guidance for Industry: Impurities: Residual Solvents, Sep. 1999, VICH GL18.
Bentz et al., Equine Vet. Educ. AE, Aug. 2000.
Fung, et al., Clin. Ther., Nov., 1996, 18(6):1037–56, abstract only.
Lindsay et al., J. Parasitol., Apr. 1995, 81(2):315–8, abstract only.
Lindsay et al., Vet. Parasitol., Sep. 20, 2000, 92(2):165–9, abstract only.
Toribio et al., J. Am. Vet. Med. Assoc., Mar. 1, 1998, 212(5):697–701, abstract only.
Janssen Research Foundation, Analytical Research PC–CHAR 89–30 (890302) –R 64433 and Safety Information for Diclazuril (no date).
Fenger, Proc. 13th ACVIM Forum, May 21, 1995, p. 597–599.
Bertone FDA Vet., May 1996, XI(III):10–13.
Stockis, J. Clin. Pharm. & Therap., 10/95, 34(8):349–2.
PubMed Natl. Libr. Med., Toltrazuril Search Results & Summary, Jan. 7, 2002, (55).
PubMed Natl. Libr. Med., Diclazuril Search Results & Summary Jan. 7, 2002, (53).

\* cited by examiner

Primary Examiner—Frederick Krass
Assistant Examiner—Donna Jagoe
(74) Attorney, Agent, or Firm—Sutherland Asbill & Brennan, LLP

(57) ABSTRACT

A composition is provided that has been specially adapted for parenteral administration, e.g., intranasal, intramuscular, subcutaneous, transdernal or intraveneous administration, wherein the composition is comprised of at least one anti-protozoal drug in a therapeutically effective amount for the treatment or prevention of protozoan infections in man and in animals. In one embodiment, the anti-protozoal drug is a triazine-based anticoccidial agent, e.g., a triazinedione or triazinetrione such as diclazuril, toltrazuril, sulfonotoltrazuril or water-soluble sodium salts thereof. In a presently preferred embodiment, the triazine-based anticoccidial agent is sulfonototrazuril. Methods of treatment of protozoal infections in man and animals are also provided.

21 Claims, No Drawings

COMPOSITIONS AND METHODS FOR PREVENTION AND TREATMENT OF PROTOZOAL DISEASE

This application claims benefit of priority in U.S. Provisional Application Serial No. 60/103,543, filed Oct. 8, 1998 and in U.S. Provisional Application Serial No. 60/112,175, filed Dec. 14, 1998.

FIELD OF THE INVENTION

The present invention relates to the treatment and prevention of diseases caused by protozoan parasites in man and in animals. In particular, the invention relates to novel compositions and methods for parenteral treatment and prevention of protozoal diseases, e.g., Piroplasmosis, Babesosis, Toxoplasmosis Neospora caninum, Crytosporidiosis and Equine Protozoal Myeloencephalitis.

BACKGROUND OF THE INVENTION

Protozoan parasites (also known as apicomplexan parasites) cause a variety of clinical disease manifestations in both man and animals. For example, hemoprotozoan parasites of the Babesia genus, namely *Babesia caballi* and *Babesia equi*, are responsible for the economically devastating disease, equine piroplasmosis. Equine piroplasmosis is widely distributed worldwide although it is most prevalent in the tropics, sub-tropics and temperate regions (see, Robinson, Edward N., "Current Therapy In Equine Medicine", Vol.2, pp.299–300, (1987) (ISBN: 0-7216-14914)).

The principal mode of transmission of the protozoan is via a tick vector, e.g., *Dermacentor nitens*. Clinical manifestation of acute infection is characterized by depression, fever, anorexia, icteric mucous membranes, ecchymotic hemorrhages and edema of the extremities and ventral abdomen. Death can occur within 24–48 hours and mortality rates in outbreaks may be high (see, Robinson, Edward, N., "Current Therapy in Equine Medicine", Vol. 3, pp. 499–500 (1992) (ISBN: 0-7216-3475-3)).

Horses which test positive for piroplasmosis (complement fixation or indirect flourescent antibody tests) are rarely allowed to enter the United States without first undergoing treatment for the disease or under rigid guidelines (see, Brooks, L., "Piroplasmosis: The Olympic Question", The Horse, pp. 43–48 (July 1996)). Currently recommended treatment regimens include the use of imidocarb dipropionate (Burroughs Welcome Co.) and often the treatment produces adverse side effects which include salivation, restlessness, colic and gastrointestinal tract hypermotility (see, Kobluk, Calvin N. et al., "The Horse Diseases & Clinical Management", Vol. 2, pp. 1084–1885 (1995) (ISBN: Vol.2 0-7216-5984-5)). Moreover, treatment with imidocarb dipropionate has met with marginal success, especially when the etiologic agent is *Babesia equi* (50% to 60%) (see, Reed, Stephen M. et al., "Equine Internal Medicine", pp. 570–571 (1998) (ISBN: 0-7216-3524-5)).

Thus, there is a need in the art for an effective antiprotozoal agent and a method of treatment and prevention of Piroplasmosis which does not produce the adverse side effects seen with current treatment regimens.

Other examples of blood borne protozoal infection caused by Babesia spp. include: babesiosis of cattle, e.g., *Babesia bigemina* and *Babesia bovis*; caprine and ovine babesiosis, e.g., *Babesia ovis*; and canine babesiosis, e.g., *Babesia canis* and *Babesia gibsoni* (see, Smith, Bradford P., "Large Animal Internal Medicine" pp.1088–1092 (1990) (ISBN: 0-8016-5062-3)). See also, Bonagura, John D. "Kirk's Current Veterinary Therapy XII Small Animal Practice", Vol. 12, pp. 315–319, (1995) (ISBN: 0-7216-5188-7)). Likewise, there is a need in the art for a safe, effective and economical treatment for such infections.

In humans, for example, protozoan infections can cause severe disease manifestations. A common sequella in patients suffering from acquired immune defficiency syndrone (AIDS) is *Cryptosporidium parvum* infection (Cryptosporidiosis) which produces severe chronic and often fatal diarrhea. The parasite is found worldwide and lives in cattle and domestic animals and is excreted in feces. It can be transmitted to humans directly from animals or through contact with feces, contaminated water or food (see, e.g. "National Institute of Allergy and Infectious Diseases—AIDS-Related Cryptosporidiosis", www press release (March, 1991)).

Many attempts have been made to find a threapeutically effective treatment for this disease. One family of drugs currently used in the veterinary profession for the treatment of coccidosis, the triazine-based anticoccidial agents (e.g., triazinediones and triazinetriones) especially diclazuril and letrazuril, have been tried experimentally in the treatment of crytosporidiosis in man (see, National Library of Medicine, AIDSDRUGS Database, DRG-0079 (Jan. 22, 1998); and (National Library of Medicine, AIDSTRIALS Database, FDA-038B (Apr. 25, 1990)). These compounds are formulated for oral administration and have met with limited success due to poor absorption. The best response to such drugs has been seen in persons with the highest blood levels post adminsitration (see, AIDS Treatment News, No. 111 (Sep. 21, 1991)).

To date, however, there is still no efficacious therapy for Cryptosporidial infections in man (see, Health Canada, Laboratory Centre For Disease Control: Material Safety Data Sheet—48, *Cryptosporidium parvum*, Oct. 11, 1997 @ (www.hc-sc.gc.calhpb/lcdc/biosafty/msds/msds/48e.html (Jul. 24, 1999)). Accordingly, there still exists an urgent need in the art for a safe and effective pareneral formulation for the treatment and prevention of potozoal infections such as cryptosporidiosis or babesiosis.

Equine protozoal myeloencephalitis (EPM), a central nervous system disease which affects equine species, is also primarily caused by a protozoan parasite, *Sarcocystis neuroma* also known as *Sarcocystis falcatula*. The horse is not a normal host for this protozoan (the horse is not part of the normal life cycle) and is considered to be a dead end host. The definitive host is thought to be the opossum. Equids are infected with the S. neuroma organisms via ingestion of food or water contaminated with feces of an infected carnivore such as the opossum (see, Robinson, Edward N., Current Therapy in Equine Medicine: Fenger, Clara A., "Equine Protozoal Myeloencephalitis", Vol. 4, pp. 329–333 (1997) (ISBN: 0-7216-2633-5)).

Recently, other protozoan parasites have been implicated as also playing an etiologic role in the pathogenesis of EPM, e.g., Neospora caninum and Toxoplasma species. Accordingly, there still exists a need in the art for an effective treatment of EPM which demonstrates broad spectrum efficacy against all protozoan parasites in the horse inclusive of the aforementioned organisms.

The clinical signs of EPM can vary from case to case. Generally, horses present neurological signs which are asymmetrical, and actual symptoms will vary depending upon the severity and location of lesions produced by the parasites in the brain, brain stem or spinal cord. Ataxia, incoordination and general weakness are usually present and can be accompanied by muscle atrophy (usually most notable in the rear limbs). There can be paralysis of the muscles of the eyes and face, drooping ears, difficulty swallowing (dysphagia) head tilt, altered gait, or even seizures and collapse. Recent reports of numbers of EPM cases indicate that the disease is far more widespread and serious than originally thought.

There is currently no vaccine available for prevention of this disease. Previously preferred treatment was aimed at control of the parasitic infection via the use of sulphonamides and pyrimethamine (see, U.S. Pat. No. : 5,747,476). However, these measures have been met with limited success. More recently, and due to the urgent need for a safe and effective treatment for this devastating disease, new methods of therapy and new agents have been explored, e.g., through the emergency FDA importation of anticoccidial agents such as diclazuril and toltrazuril (see, FDACVM publication: "Instructions for Personal Use Importation of Diclazuril" (Dec. 16, 1997); and FDACVM publication: "The Importation of Toltrazuril for Personal Use" (1997) which are available from the American Association of Equine Practitioners, Lexington, Ky. (AAEP)). (See also, U.S. Pat. No.:5, 883,095).

It should be noted that the current emergency importation and treatment of horses with diclazuril and toltrazuril is speculative. Oral formulations adapted for use in the horse of one or more of these drugs are currently in clinical trials for FDA approval. And, while some horses do dramatically improve, many only see moderate improvement (improve 1–2 grades on the clinical evaluation scale (ranging in grades of 1–5) used by veterinarians to classify the severity of clinical signs). The test dose for a presently preferred form of toltrazuril, the metabolite toltrazuril sulfone (Bayer) is currently 5 mg/kg up to 10 mg/kg per day for the FDA trials.

The cost for importation and use of the above anticoccidials ranges anywhere from about $800–$1,200.00 per horse and results obtained from the treatment can be disheartening. Few horses experience complete recovery from any known conventional therapy, including the triazine-based anticoccidial therapies which are mentioned above. Moreover, the relatively high levels of drug recommended in the therapeutic regimen can produce unwanted side effects. This is especially true for treatment regimens which utilize sulfonamides and pyrimethamine which inhibit folic acid production (see, Fenger, Clara A., "Update on the Diagnosis of Equine Protozoal Myeloencephalitis (EPM)" Proc. 13$^{th}$ ACVIM Forum, pp.597–600 (1995); and Bertone, Joseph J., "Update On Equine Protozoal Myeloencephalitis", FDA Veterinarian, Vol. XI, No. III (May/June 1996)).

Therefore, there exists a need in the art to provide a safe and more effective method of parenteral treatment of EPM which is also less costly.

SUMMARY OF THE INVENTION

The present invention satisfies the need in the art by providing a composition containing at least one anti-protozoal drug especially adapted for parenteral administration, e.g., intranasal, intramuscular, subcutaneous, transdermal or intravenous administration, for the treatment and prevention of protozoan infections in man an in animals. In one embodiment, the anti-protozoal drug is a triazine-based anticoccidial agent, e.g., a triazinedione or triazinetrione such as diclazuril or toltrazuril. In a presently preferred embodiment, the triazine-based anticoccidial agent is sulfonotoltrazuril.

The compositions of the invention can further comprise a suitable solvent for the anti-protozoal drug in a formulation specially adapted for a particular route of parenteral administration. The choice of solvent and concentration of active dissolved therein will of course vary depending upon the choice of drug, the desired route of parenteral administration, the species and host being treated, and the desired duration of action of the administration, e.g., sustained release vs. loading dose.

Parenteral administration of the compositions of the invention reduces the dosage amount of drug by about one fold to as much as one hundred fold but especially about five fold compared with oral dosing. The compositions provided by the invention eliminate the variability in plasma concentrations of the drug due to animal to animal differences in oral bioavailability, allow use of a loading dose and therefore immediate attainment of effective plasma concentrations of the drug, allow rapid attainment of high plasma concentration of the drug to drive the drug into extravascular compartments such as the cerbrospinal fluid in the CNS, provide better and more immediate control of the plasma concentration of the drug and reduce the potential for side effects related to the currently existing oral formulations. As a result, the cost of treatment is greatly reduced along with the potential for adverse side effects as seen from higher doses currently recommended and needed for oral administration of these anti-protozoal drugs.

In particular, the present invention provides novel compositions and methods for the treatment and/or prevention of any anti-protozoal or apicomplexan parasite in man and animals, e.g. equine piroplasmosis, equine protozoal myeloencephalitis and Cryptosporidiosis. In one embodiment, the invention provides a composition comprised of a triazine-based anticoccidial drug and a suitable solvent useful for the treatment of anti-protozoal infections. A preferred embodiment of the invention comprises a composition comprised of diclazuril in solution with DMSO, DMA or mixtures thereof which is formulated for parenteral administration for the treatment of anti-protozoal infection in man or in animals as provided by the methods of the invention.

Another preferred embodiment of the invention comprises a composition comprised of toltrazuril, toltrazuril sulfone, sulfonotoltrazuril or mixtures thereof in solution with DMSO, DMA or mixtures thereof which is formulated for parenteral administration for the treatment of anti-protozoal infection in man or in animals as provided by the methods of the invention.

Yet another preferred embodiment of the invention comprises a composition formulated for parenteral or oral administration for treatment of anti-protozoal infections in man and in animals comprised of a soluble salt, e.g., a sodium salt, of a triazine-based anticoccidial agent, e.g., clazuril, diclazuril, letrazuril, toltrazuril, toltrazuril sulfone, or sulfonotoltrazuril and the like.

Also provided by the invention is a method for preparation of water-soluble forms of triazine-based anticoccidial agents, e.g., clazuril, diclazuril, letrazuril, toltrazuril, toltrazuril sulfone, or sulfonotoltrazuril for use in the methods of treatment of anti-protozoal infections provided by the invention.

DETAILED DESCRIPTION OF THE INVENTION

The present invention provides a composition and method for the parenteral treatment of protozoan (apicoplexan)

infections in man and in animals. The protozoan parasite can be any protozoan known to infect man or animals, including, but not limited to, e.g., Babesia spp. Sarcocystis spp. Neosporum spp. Crytosporidium spp. Toxoplasma spp. and the like.

It is contemplated that the compositions of the invention can be formulated for any parenteral administration. It is specifically contemplated that intravenous, intramuscular, transdermal, intranasal and subcutaneous routes of administration can be utilized for administration of the compositions of the invention. Specific formulations of the compositions of the invention can include powders, gels, ointments, creams, solutions, suspensions, sustained release preparations, patches and the like.

In one embodiment, the invention provides a composition specially adapted for intravenous, intramuscular, subcutaneous, or intranasal administration which is useful for the treatment of a protozoal infection in man or in animals, e.g., for treatment of equine piroplasmosis, equine protozoal mycloencephalitis or human cyrptosporidiosis infection, wherein the composition comprises at least one chemical agent which has anti-protozoal activity. The compositions provided herein can include any anti-protozoal agent, but especially anti-coccidial agents such as any of the class of triazine-based anti-coccidial agents (i.e., agents which contain a triazine ring, e.g., the 1, 2, 4 triazine ring or the 1, 3, 5 triazine ring configurations (see, e.g. "A 3D-QSAR Study of Anticoccidial Triazines Using Molecular Shape Analysis", *J. Chem. Inf. Comput Sci.*, Vol. 35, 771–778 (1995); U.S. Pat. No. 4,837,216; and U.S. Pat. No. 4,952,570, the contents of which are incorporated herein by reference).

Specific examples of such agents include, but are not limited to, clazuril, diclazuril, toltrazuril, toltrazuril sulfone, or sulfonotoltrazuril. For example, the chemical structures of several triazine-based compounds useful in the compositions and methods set forth herein are shown below:

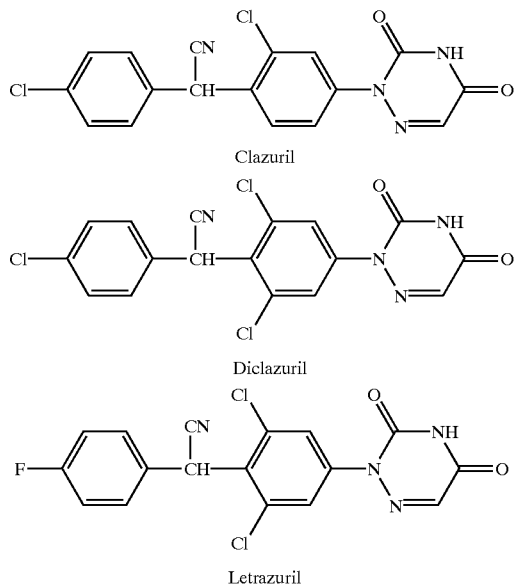

-continued

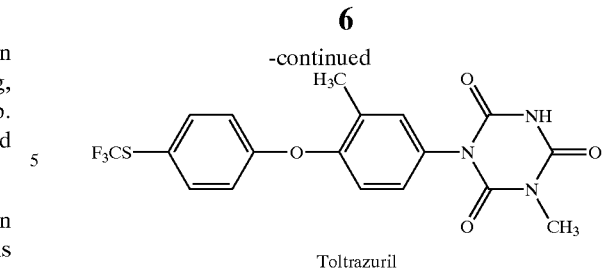

Toltrazuril

It can be appreciated that other anti-protozoal agents including their derivatives, analogs, isomers, salts, and natural metabolites of these agents can also be utilized in the compositions for parenteral treatment and prevention of any protozoal infection in man or in animals. In a presently preferred embodiment, the triazine-based anticoccidial agent is sulfonotoltrazuril, a toltrazuril metabolite.

Sufonotoltrazuril, the toltrazuril metabolite, contains the thio group of toltrazuril that has been oxidized to a sulfono group thereby differing toltrazuril from its dioxo sulfonotoltrazuril derivative.

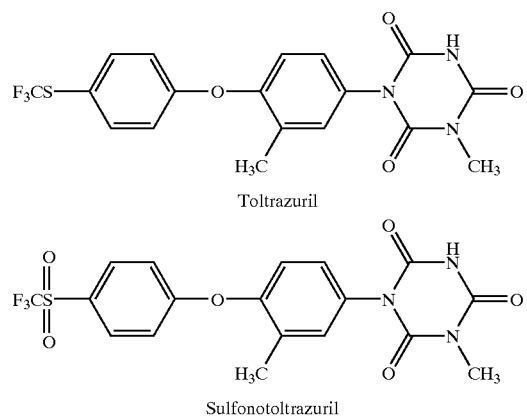

The chemical name used in the Chemical Abstract Database for one form of the sulfonotoltrazuril contemplated by the invention is: 1-methyl-3-[3-methyl-4-(4-trifluoromethanesulfonyl-phenoxy)-phenyl]-[1,3,5]triazinane-2,4,6-trione.

The CAS catalog number of this compound is CAS No. 69004-04-2. The Beilstein Registry Number is 870959. The Molecular Formula is $C_{18}H_{14}F_3N_3O_6S$ and the Molecular Mass is 457.38 g/mol.

In particular, the invention provides a composition which is useful for parenteral treatment and/or prevention of EPM which utilizes between about ¼th to about ¹⁄₁₀₀th of the amount of an anti-protozoal drug which is necessary for oral administration in the treatment of EPM. In one embodiment of the invention, the compositions are adapted for intranasal administration and comprise about ¹⁄₁₀th of the currently recommended dosage. In another embodiment, the compositions are adapted for other parenteral administration (e.g., intravenous, subcutaneous and intramuscular) and comprise between about ¼th to about ¹⁄₁₀₀th of the currently recommended oral dosage, but especially about ⅓rd to about ¹⁄₁₀th of the currently recommended oral dosage for EPM treatment. In a preferred embodiment, the intranasal and parenteral compositions of the invention set forth above are formulated for sustained release as set forth in greater detail below.

For example, the currently recommended dosage for oral diclazuril (CLINACOX®, Pharmacea Upjohn, Canada) in the horse for an EPM treatment regimen is about 2.5 grams of diclazuril per 1000 pound horse per day (5.5 mg/kg) administered once daily for 28 days. This amounts to about 70 grams of diclazuril per horse per treatment regimen.

By contrast, the presently preferred dosage range for the parenteral compositions of the present invention for treatment of EPM which are comprised of similar triazine-based agents, e.g., diclazuril or toltrazuril and the like, is from between about 0.1 mg/kg to about 10 mg/kg. However, the skilled artisan can appreciate that this range can vary from between about 0.01 mg/kg to about 20 mg/kg depending upon the specific formulation, route of administration, the desired effect (loading dose vs. sustained release) and the duration of the treatment regimen.

A presently preferred embodiment of the invention comprises a composition adapted for parenteral administration wherein the anti-protozoal agent is selected from, but not limited to the group consisting of clazuril, diclazuril, letrazuril, toltrazuril, toltrazuril sulfone, and sulfonotoltrazuril or a sodium salt thereof and a suitable solvent. The solvent can be any suitable solvent for use in animals and man and will, of course vary depending upon the choice of anti-protozoal agent and the route of administration. Presently preferred solvents include, but are not limited to DMSO, DMA, ethanol, water and the like as set forth more fully below.

The preferred compositions can be utilized in methods of treatment of anti-protozoal infections in man and in animals. For example, a presently preferred treatment regimen for treatment of EPM comprises administering to a 1000 lb horse a composition for intravenous administration comprised of between about 50 mg to about 1,500 mg , but especially between about 250 mg and about 1000 mg and most preferably about 500 mg (about 1.1 mg/kg) of diclazuril, toltrazuril, toltrazuril sulfone or sulfonotoltrazuril dissolved in a suitable volume of DMSO, DMA or the like. Suitable amounts of solvent will vary from between about 2 ml to about 30 ml per unit dose depending upon the choice of the anti-protozoal agent and the choice of solvent. According to the methods set forth herein, the composition can given once per day (SID) for a duration of between about 10 and about 35 days but especially between about 20 and about 30 days and most preferably about 28 days. Alternatively, a loading dose of the composition can be given to achieve rapid critical plasma concentrations on day one of the regimen followed by a maintenance dose (see, Example 1 below) for a shorter duration of therapy, e.g., between about 15 and about 25 days.

In yet another embodiment, the compositions can be specially formulated for parenteral use, e.g., intramuscular or subcutaneous, sustained release, e.g., a microsphere or methylcellulose preparation such that a single sustained release administration or a weekly administration of sustained a sustained release fonrulation of the anti-protozoal agent is possible. Alternatively, a single intravenous loading dose followed by a sustained release intramuscular or subcutaneous dose for maintaining sustained critical blood levels is contemplated. In EPM, for example, the critical plasma concentration can range from about 5 µg/ml of the antiprotozoal agent to about 12 µg/ml, but especially about 8 µg/ml.

INTRAVENEOUS ADMINISTRATION EXAMPLES

Example #1

"Mr. Owens" and Single IV Administration of Diclazuril

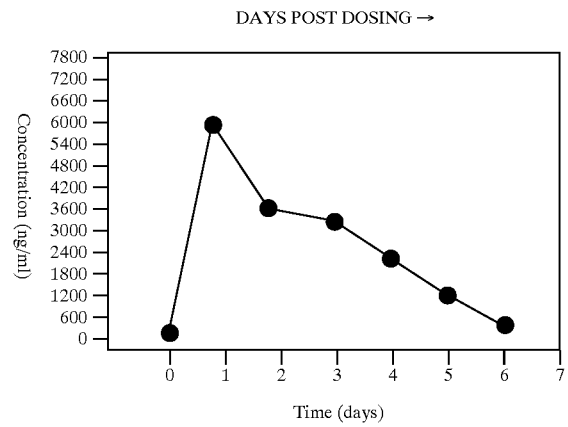

As set forth in Table 1 above, the horse MR. OWENS, (about 1,000 lbs.) received 750 mg of diclazuril powder dissolved in 30 ml of DMSO, intravenously, twice on day one, at zero and zero plus one hours for a total dose of 1,500 mg. Blood samples were drawn at the indicated time points immediately before the next dosing and the solid circles (●—●)

in FIG. 1 represent plasma concentrations of diclazuril after these administrations. Plasma concentrations of dicalzuril in ng/ml are represented on the vertical axis against time in days on the horizontal axis. Note the 6,000 ng/ml of diclazuril peak blood level at 24 hours after dosing, and the approximately 48 hour plasma half-life, consistent with previously reported data on the plasma half-life of dicalzuril in the horse.

Example #2

"Deep Powder" and Repeated Daily IV Administration of Diclaxuril

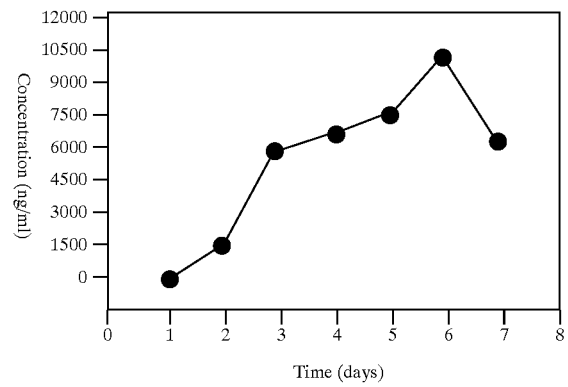

The horse, DEEP POWDER, 1160 lbs., in Table 2 above was administered diclazuril at a dose of 0.5 mg/lb. (580 mg)

in DMSO IV once a day for eight days. Plasma levels of diclazuril at 24 hours after each dose administration and just before the next day's dosing are represented by the solid circles (●—●)

in the above Table 2. Note bow the dose of 580 mg/1,000lbs/day yields a stepwise increasing plasma concentrations of diclazuril, yielding a final steady state plasma concentration of diclazuril of about 10,000 ng/ml. Note also the close comparison between these data and data previously presented on CLINICOX®, where daily oral administration of about 2.5 g/1,000 lbs. of diclazuril as CLINICOX® yielded broadly similar data. The data show that IV administration of about 0.5 mg/1,000 lbs. of dicalzuril in DMSO produced equivalent plasma concentrations of diclazuril as about five times this dose of CLINICOX® orally, suggesting about 20% or less oral bioavailability of this agent.

Example #3

"Loading Dose" Effect and Expected Therapeutic Benefits

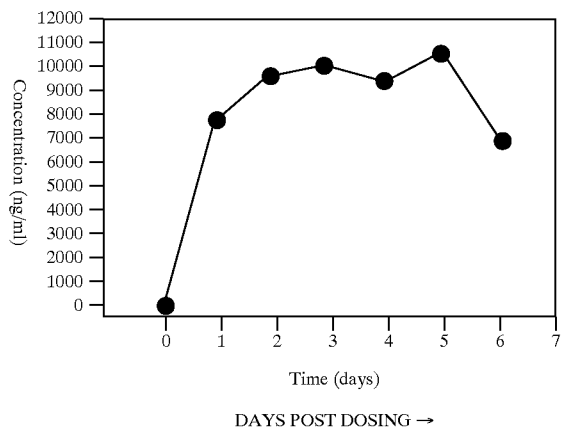

DAYS POST DOSING →

Pharmacokinetics and the summation principle teaches us that administration of a loading dose such as that presented in Example 1, MR OWENS, followed by a daily maintenance dose such as that presented in Example 2, DEEP POWDER, should allow rapid attainment and maintenance of a desired or therapeutically optimal plasma concentration of (about 8–10 μg/ml in plasma) diclazuril. Table 3 above shows the estimated plasma levels that would be obtained in horses of the approximately 1,000 lb. body weights of MR. OWENS and DEEP POWDER if the 1,500 mg loading dose was administered on day I, followed by daily maintenance doses of 500 mg day as was administered to DEEP POWDER. In this way, and following these general protocols and principles, it would be possible to rapidly attain full effective plasma concentrations of diclazuril or a related agent on day one of treatment and maintain these effective concentrations for any desired period of time.

The advantages of this approach are many fold: In the first place, effective plasma and cerebrospinal fluid concentrations of diclazuril or a similar agent are attained within hours or minutes of the start of treatment, which can lead to shorter treatment periods. In the second place, the required plasma concentrations can be maintained by the administration of only about one fifth or less of the total drug amount that must be administered orally, based on our experience with CLINICOX® administration, which may lead to substantial savings on drug costs. Thirdly, the significant horse to horse variability in bioavailability of this agent and the resulting variability in plasma concentrations of diclazuril found after oral administration can be avoided, leading to more predicable and reproducible treatment results. Fourthly, using this methodology, very high plasma concentrations of diclazuril can be rapidly attained, leading to equivalently rapid entry of diclazuril into the CNS and to equivalently rapid anti-protozoal actions in the CNS. Fifthly, the optimal plasma concentrations of diclazuril to treat this disease and the optimal duration of therapy and most cost effective therapeutic approaches to EPM have yet to be conclusively established.

This IV approach to administration of diclazuril, by allowing precise control of drug concentrations and rapid entry of drug into the CNS, provides a tool necessary to precisely control the plasma levels of the drug and cerebrospinal fluid concentrations of this agent to obtain this information. Sixth and finally, the fact that IV administration exposes the horse to less of this drug and to none by the direct intestinal route reduces the probability of adverse effects developing relating to the gastrointestinal system and also to other body systems of the horse.

Example #4

Mr. Owens / Clinacox Data: Pharmacokinetic Analysis and Bioavailability Calculations

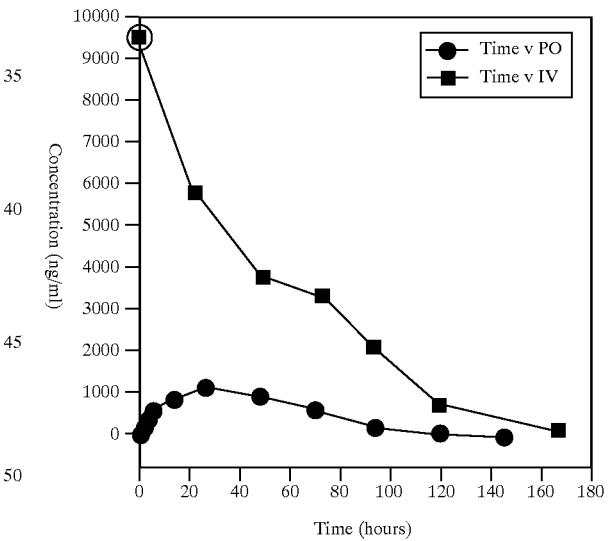

Pharmacokinetic analysis of the data obtained after IV administration of this drug and comparison with previously reported pharmacokinetic data after administration of CLINICOX® (Table 4 above) shows that the estimated oral bioavailability of CLINICOX® may be actually less than the earlier estimated 20%. In Table 2, the intravenous data from MR. OWENS (solid squares (solid squares ■—■)

is plotted along with the previously obtained CLINICOX®oral administration data (solid circles ●—●)

and subjected to pharmacokinetic analysis as set forth below. These data suggest that the bioavailability of orally administered CLINICOX® is about 13% less that the figure developed in the experiments presented above.

Example #4

Mr. Owens / Clinacox Data: Pharmacokinetic Analysis and Bioavailability Calculations / Continued Following oral administration, concentration of diclazuril at 120 hours was considered as outliers.

Area Under the Curve (AUC from 0 to ∞): Trapezoidal rule was used to calculate area under the curve for oral drug administration.

$$AUC\ t_1\ to\ t_2 = \frac{C1 + C2}{2}(t_1 - t_2)$$

$$AUC\ t_{last}\ to\ t_\infty = \frac{Clast}{k}$$

First order process: $k = \frac{LnC_1 - LnC_2}{t1 - t2}$  $k = 0.0164\ hr^{-1}$ $AUC$ from 0 to ∞ $(PO) = 98.2$ μg/ml/hr Concentrations at 72 hr and 96 hr were not included in calculation following IV administration.

Area Under the Curve (AUC from 0 to ∞): Intercept-Slope Method $$AUC\ (AUC\ from\ 0\ to\ \infty)(IV) := \frac{C_0}{k}\ \ k = 0.021\ hr^{-1}$$

AUC (AUC from 0 to ∞) (IV): 452.4 μg/ml/hr $$F(\text{Bioavailability}) = \frac{98.2}{457.4}\ \frac{\text{IV dose } 1.5}{\text{PO dose } 2.5}$$

F=13%

$$V(\text{volume of distribution}) = \frac{Dose}{Co}\ \frac{1.5\ g}{9.6\ \mu g/ml}\ \ V = 0.35\ L/kg$$

$$Cl(\text{systemic clearance}) = \frac{Dose}{AUC\ 0\ to\ \infty}\ \frac{1.5\ g}{452.4\ \mu g/ml/hr}$$

Cl=55.26 ml/min.

Not detectable level of diclazuril in urine samples by both HPLC and TLC methods suggested that hepatic clearance is the major elimination route for diclazuril in horses.

$Cl_H = Q_H \cdot E_H$

EH is lower than 0.3 so diclazuril is found to have low hepatic extraction ratio.

In yet another embodiment of the invention, the above-described preferred compositions can be utilized in methods of treatment of anti-protozoal infections in animals other than EPM. For example, a presently preferred treatment regimen for treatment of Piroplasmosis in horses comprises administering to a 1000 lb horse a composition for intravenous administration comprised of between about 50 mg to about 1,500 mg, but especially between about 250 mg and about 1000 mg and most preferably about 500 mg (about 1.1 mg/kg) of diclazuril, toltrazuril, toltrazuril sulfone or sulfonotoltrazuril dissolved in a suitable volume of DMSO, DMA or the like. Suitable amounts of solvent will vary from between about 2 ml to about 30 ml per unit dose depending upon the choice of the anti-protozoal agent and the choice of solvent. According to the methods set forth herein, the composition can given once per day (SID) for a duration of between about 1 and about 20 days but especially between about 1 and about 10 days and most preferably about 4 days. Alternatively, a loading dose of the composition can be given to achieve rapid critical plasma concentrations on day one of the regimen followed by a maintenance dose for a shorter duration of therapy, e.g., between about 2 and about 10 days. In yet another embodiment, the compositions can be specially formulated for sustained release as set forth below such that a single administration of the anti-protozoal agent is possible or, alternatively a single intraveneous loading dose followed by an intramuscular or subcutaneous dose for sustained critical blood levels.

As set forth above, clazuril, diclazuril, toltrazuril, toltrazuril sulfone and sulfonotoltrazuril as well as other triazine-based anti-coccidials agents that are useful in the prophylaxis and therapy of equine protozoan myeloencephalitis (EPM) and other protozoal diseases in man and animals. These compounds are hydrophobic and highly water insoluble.

Prior to the teachings set forth herein, there had been no suitable water soluble formulation for parenteral administration of these agents. Accordingly, the present invention provides compositions comprised of a water-soluble form of at least one anti-protozoal agent which is useful for the treatment of a protozoal infection in man or in animals and a method for making such a composition. In a presently preferred embodiment, the composition is comprised of the sodium salt of one or more triazine-based anticoccidial agents, including, but not limited to clazuril, diclazuril, letrazuril, toltrazuril, toltrazuril sulfone, sulfonotoltrazuril or mixtures thereof.

A presently preferred way to increase the water solubility of such drugs is to make their salt forms. Clazuril, diclazuril, toltrazuril, toltrazuril sulphone and sulfonotoltrazuril are weak acids because of the imide hydrogen present in all five compounds as shown below. The anion formed when this hydrogen gets abstracted is resonance stabilized. Thus, these acidic compounds can be reacted with a base to form the corresponding salt and water in a typical acid-base titration reaction. For instance, the sodium salt of diclazuril was formed by reacting diclazuril with sodium hydroxide as set forth below in a 1:1 molar ratio.

Synthesis of the sodium salt of diclazuril

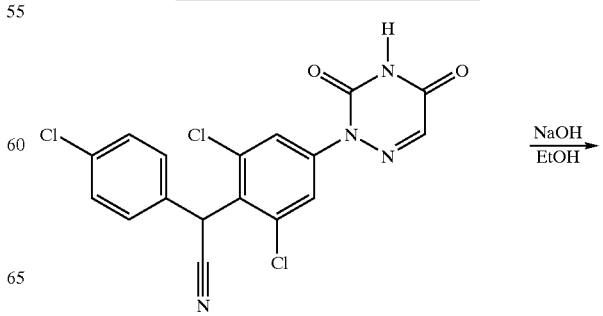

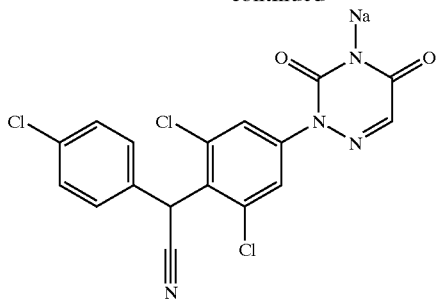

+ H₂O

Evidence for Salt Formation:

1. Molar ratio of sodium hydroxide required for compete titration of diclazuril was 1:1.
2. The salt dissolves immediately in water while diclazuril is completely insoluble in water.
3. Diclazuril is a white powder. The sodium salt of diclazuril has a brownish tan color.
4. Mass spectral analysis in the negative mode of the sodium salt of diclazuril and diclazuril itself was conducted. The expected molecular weight of the molecular anion of the salt and the parent compound is 404.971. The measured molecular weight matched exactly to the expected weight (Data not shown).

Therefore, clazuril, diclazuril, toltrazuril, toltrazuril sulphone, and sulfonotoltrazuril, as well as certain other triazine-based anticoccidials, have in common an acidic imide hydrogen which allows for an acid-base titration reaction with a base to give the corresponding salts and water. This was demonstrated with the synthesis of the sodium salt diclazuril as set forth more fully in Example 5 below. Give the teachings provided herein, it can be appreciated that other alkali bases including, but not limited to Ca(OH)$_2$, KOH, LiOH can also be used.

Example #5

Synthesis of a Water-soluble Salt of Diclazuril

Diclazuril has a very low solubility in water (<1×10$^{-7}$ at pH 6.5) and can in fact be considered as practically-insoluble in water. A presently preferred plasma drug concentration of about 8 μg/ml for about 25–30 days is needed for the effective treatment of equine protozoan myeloencephalitis (EPM). The oral bioavailability of diclazuril is very low. Thus, a parenteral formulation is desired.

One of the methods to increase the water solubility of poorly water-soluble drugs is to make water-soluble salts of the drug. Diclazuril can be considered as a weak acid because of the presence of the imide hydrogen as shown below:

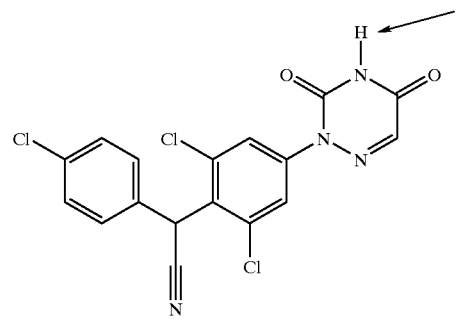

Structure of Diclazuril with Arrow Indicating the Acidic Imide Hydrogen

The anion formed when this acidic hydrogen gets abstracted is stabilized by resonance below:

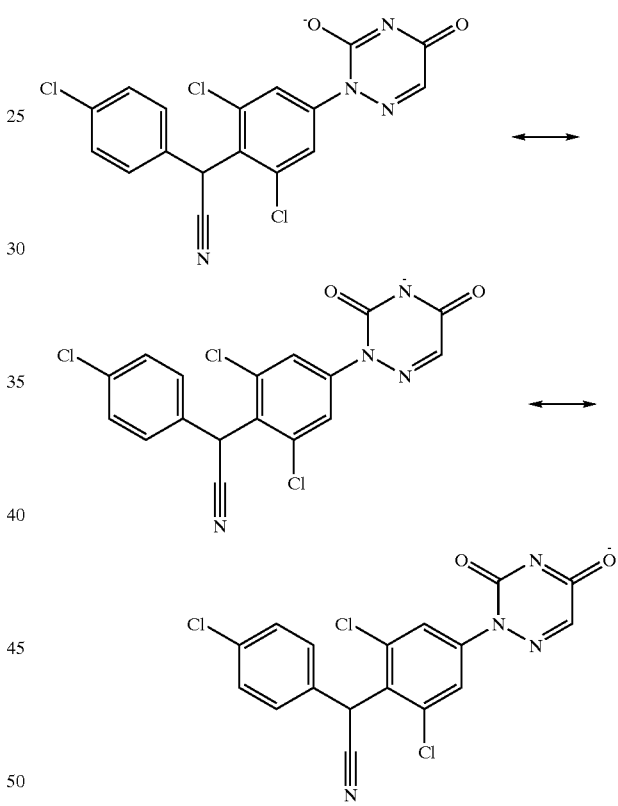

Resonance Structures of Diclazuril Imide Anion

Since diclazuril is a weak acid, it can react with a base to give a salt and water. NaOH was chosen as the presently preferred base and an acid-base reaction was carried out wherein I gram of diclazuril was suspended in 50 ml of ethanol in a 200 ml volumetric flask. To this, phenolphthalein indicator was added to indicate equivalence point of titration. A buret was filled with 1 M NaOH. The base was slowly added from the buret to the solution. The titration was stopped when a change in the color of the phenolphthalein indicator (colorless to pink) was observed. At the equivalence point, it was observed that the white milky suspension of diclazuril had changed to a clear pink solution. This was thought to be due to the conversion of the acid to the salt.

The solution was re-crystalized by evaporation in an oven set at 75° C. for two hours.

Synthesis of sodium salt of diclazuril

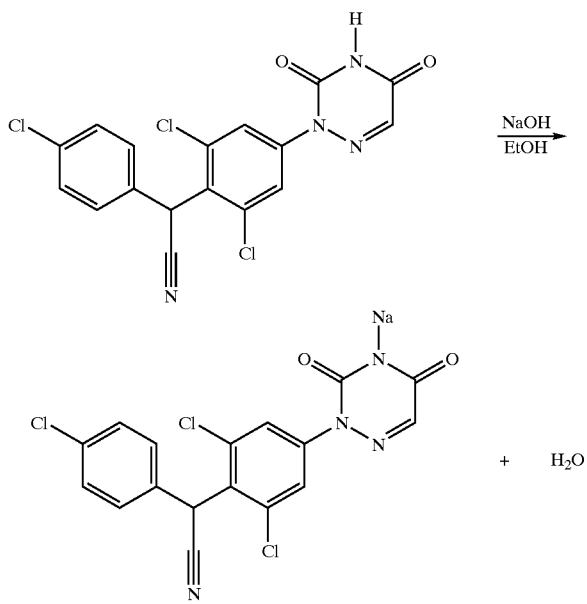

Calculation of moles of NaOH required to titrate 1 mole of diclazuril indicated that the molar ratio was 1:1, suggesting acid-base reaction and thus salt formation.

While it is possible that the nitrile and imide functional groups can be hydrolyzed by a base. This probably does not occur, however, because hydrolysis of nitrites and imides requires more severe conditions including refluxing for several hours. In addition, the reaction was conducted in ethanol thereby eliminating water required for the hydrolysis reaction.

Evidence for Salt Formation
1. The titration experiment strongly suggests acid-base reaction.
2. Mass spectral evidence: Fourier transform matrix-assisted laser desorption ionization mass spectrometry (MALDI-FTMS) with dithranol matrix was used to measure the mass spectra of diclazuril starting material and diclazuril free acid obtained from the sodium salt of diclazuril. The expected molecular weight of diclazuril anion ($C_{17} H_8 C_{13} N_4 O_2^-$) is 404.972. The measured molecular weight is 404.971. Isotopic peaks arising from chlorine were measured at m/z of 406.967 and 408.965. A cluster of peaks at molecular weight 333.971 in the spectrum corresponds to a fragment peak of the molecular ion formed after the loss of two chlorine atoms. The sodium salt was converted to the free acid by extraction with ethyl acetate and treatment with acetic acid prior to mass spectral measurement. Again, the expected molecular ion of diclazuril anion is 404.972 and the measured molecular weight of 404.971 matched exactly to the expected weight. Isotopic peaks arising from primarily from chlorine were also measured. Cluster of peaks seen at 333.971 again corresponds to a fragment peak obtained after the loss of two chlorine ions. An additional cluster of peaks at molecular weight 395.952 that was not seen in the mass spectrum of diclazuril starting material was seen in the mass spectrum of diclazuril free acid obtained from the sodium salt. This peak is thought to be either an unidentified fragment peak of the molecular ion, peak arising from impurities or minor side product of the titration reaction. Further analysis by HPLC is warrented to identify whether this peak is a fragmentation product or an impurity.

pH Stability of Sodium Salt of Diclazuril

The manufacturer of diclazuril, JANSEEN Research Foundation, listed the pKa of diclazuril to be 5.92 in its physico-chemical characteristics of diclazuril. It can be expected that at pH's above the pKa of the compound (i.e. pH>6), aqueous solution of diclazuril would stay in solution. Preliminary studies were conducted to determine the pH at which sodium salt would precipitate.

Sodium salt of diclazuril was dissolved in water. It went into solution almost immediately. The pH of the aqueous solution was 12.4. To this solution, 1N HCl was added dropwise while stirring and the pH at which the solution began to turn cloudy was recorded. This pH was found to be 10.5. This would indicate that the pKa of diclazuril is not 5.92 as indicated by JANSEEN but closer to 10.5. Actually, a check of reference pKa's of organic compounds shows that imides have a pKa in the range of 8.3–9.6.

The result of the pH stability study indicated that aqueous formulation of sodium salt of diclazuril has to be formulated preferably at a higher pH close to 11 to ensure that the drug stays in solution. This will not cause a problem as there are many drugs on the market that are formulated at higher pHs for exactly the same reason.

Accordingly, the present invention provides a composition useful for the treatment of a protozoal infection in man or in animals comprised of a water-soluble form of a triazine-based anticoccidial including, but not limited to, clazuril, diclazuril, toltrazuril, toltrazuril sulfone and sulfonotoltrazuril. In a presently preferred embodiment of the invention, the water soluable triazine-based anticoccidial is a sodium salt of clazuril, diclazuril, toltrazuril, toltrazuril sulfone, sulfonotoltrazuril or a mixture thereof.

The preferred compositions can be utilized in methods of treatment of anti-protozoal infections in man and in animals. For example, a presently preferred treatment regimen for treatment of EPM comprises administering to a 1000 lb horse a composition for intraveneus administration comprised of between about 50 mg to about 1,500 mg, but especially between about 250 mg and about 1000 mg and most preferably about 500 mg (about 1.1 mg/kg) of a water-soluble sodium salt of diclazuril, toltrazuril, toltrazuril sulfone or sulfonotoltrazuril dissolved in a suitable volume of water or stored in a freeze-dried preparation for admixing with a suitable amount of sterile water for injection at the time of utilization. Suitable amounts of water for the composition will vary from between about 2 ml to about 30 ml per unit dose depending upon the choice of the anti-protozoal agent and the parenteral route of administration.

According to the methods set forth herein for EPM treatment, the composition can given once per day (SID) for a duration of between about l0 and about 35 days but especially between about 20 and about 30 days and most preferably about 28 days. Alternatively, a loading dose of the composition can be given to achieve rapid critical plasma concentrations on day one of the regimen followed by a maintenance dose (see, Example 1 above) for a shorter duration of therapy, e.g., between about 15 and about 25 days.

It is also specifically contemplated that the water-soluble forms of the triazine-based anticoccidials provided herein can be utilized in suitable oral formulations for treatment and prevention of protozoal infections and infestations in man and in animals. The solubility of the compositions provided herein greatly enhance the oral bioavailability of the active anti-protozoal agent and accordingly lessen the dosage requirement to roughly the equivalent of that of the parenteral formulations. Given the teachings provided herein, the skilled artisan can optimize the dosage requirements and the therapeutic regimen for a particular formulation depending upon the condition being treated or prevented and the species of animal.

One embodiment of the present invention provides a composition useful for the treatment of a Cryptosporidium spp. infection especially in man or in animals comprised of a water-soluble form of a triazine-based anticoccidial including, but not limited to, clazuril, diclazuril, toltrazuril, toltrazuril sulfone or sulfonotoltrazuril. In a presently preferred embodiment of the invention, the water soluable triazine-based anticoccidial is a sodium salt of clazuril, diclazuril, toltrazuril, toltrazuril sulfone, sulfonotoltrazuril or a mixture thereof and can be used parenterally or orally in a therapeutic treatment regimen. It is also contemplated that the above-described compositions comprised of a triazine-based anticiccidial and a suitable solvent, e.g., DMSO or DMA, can be utilized parenterally to treat Cryptosporidium spp. infection in man or in animals.

For example, a presently preferred treatment regimen for treatment of Cryptosporidium spp. infection comprises administering to an approximately 200 lb human subject from between about 10 mg to about 400 mg, but especially between about 25 mg and about 300 mg and most preferably about 200 mg (about 1.1 mg/kg) of a water-soluble sodium salt of diclazuril, toltrazuril, toltrazuril sulfone or sulfonotoltrazuril dissolved in a suitable volume of water or stored in a freeze-dried preparation for admixing with a suitable amount of sterile water for injection at the time of utilization. Suitable amounts of water for the composition will vary from between about 2 ml to about 10 ml per unit dose depending upon the choice of the anti-protozoal agent and the route of route of administration. It can certainly be appreciated that the oral formulations of the water-soluble salts of these agents can be in a liquid, semi-solid or solid form as a pill tablet, elixir and the like.

Current recommendations for treatment of EPM with pyrimethamine and a sulfonamide are set forth in the above-cited articles by Dr. Clara Fenger (1995) and Dr. Joe Bertone (1995 which are hereby incorporated by reference. Accordingly, in yet another embodiment of the invention, the composition is comprised of at least one anti-protozoal agent as set forth above and can also comprise a reduced amount of a sulfonamide and/or pyrimethamine for the parenteral, e.g., the intranasal formulations.

One skilled in the art can appreciate that depending upon the compound which is selected as the therapeutic agent, the method of solubilization of the compound for inclusion in the composition provided herein can vary and can be readily ascertained based upon known chemical properties of the selected compound, as found, e.g., in the material safety data sheets (MSDS) for the particular compound or via known methods of synthesis etc. In particular, methods for solubilization of the active compound and formulation of compositions that are specially adapted for intranasal administration are known as set forth, e.g., in U.S. Pat. Nos.: 4,284,648, 4,428,883; 4,315,925 and 4,383,993, the contents of which are hereby incorporated by reference.

In view of the mixed results of the cases of EPM treated to date by the oral route, it is very surprising that by utilizing a different route of administration (i.e., intranasal) and decreasing the dose, that one could achieve better results, especially when using an anti-coccidial agent which has to exert its effect on the organism in the horse. Furthermore, while the solubilization techniques suggested above were known, it has not been heretofore suggested that such can be used for solubilizing triazine-based anti-coccidial agents, such as diclazuril, toltrazuril, and toltrazuril sulfone, in order to provide compositions for intranasal administration. The intranasal route allows for direct absorption of drug through the nasal mucosa and directly across the blood brain barrier into the CSF without first having to pass through the liver. This may produce the unexpectedly better result seen with this route of administration, even with drastically lower unit dosages of drug.

For example, one embodiment of the invention utilizes a composition for treatment of EPM adapted for intranasal administration which is comprised of toltrazuril, toltrazuril sulfone or sulfonotoltrazuril in a therapeutically effective amount in which the unit dose is less than the unit dose required for a therapeutically amount of toltrazuril, toltrazuril sulfone or sulfonotoltrazuril as is normally required for oral administration of either drug. In preferred embodiments, the therapeutically effective amount of the compositions comprised of toltrazuril, toltrazuril sulfone or sulfonotoltrazuril is between about 1/4th and 1/100th but especially about 1/10th of the therapeutically effective amount of toltrazuril, toltrazuril sulfone or sulfonotoltrazuril that is required for oral administration. Currently recommended oral dosage levels of toltrazuril, toltrazuril sulfone or sulfonotoltrazuril are 5–10 mg/kg per unit dose administered once daily orally such that a typical 500 kg horse would receive between about 2.5 to about 5 grams of active ingredient per day.

Thus, one presently preferred embodiment of the invention comprises a composition comprised of toltrazuril, toltrazuril sulfone or sulfonotoltrazuril in solution with N-methyl-glucamine and water. For instance, a typical example of how to solubilize toltrazuril for use in the compositions contemplated by the invention is to combine about 10 mg of toltrazuril with about 100 mg of N-methyl glucamine and about 10 cc of water. One can appreciate given the known properties of toltrazuril, toltrazuril sulfone or sulfonotoltrazuril that other solvents can be utilized for use in preparation of the above compositions.

In one embodiment of the invention, the effective amount of toltrazuril, toltrazuril sulfone or sulfonotoltrazuril per unit dose for intranasal administration is between about 50 mg and about 1,500 mg, but especially between about 100 mg and about 750 mg. In one embodiment, the effective amount of toltrazuril, toltrazuril sulfone or sulfonotoltrazuril per unit dose is about 500 mg. Depending upon the dosage required for either treatment or prevention of EPM (which can be optimized utilizing methods known in the art) the appropriate amount of toltrazuril or sulfonotoltrazuril can be solubilized for production of a unit dose or the unit doses can be combined in a multiple treatment vial or container.

Likewise, another embodiment of the invention provides a composition adapted for intranasal administration which is comprised of diclazuril in a therapeutically effective amount in which the unit dose is less than the unit dose for a therapeutically amount of diclazuril that is required for oral administration to treat EPM. In preferred embodiments, the therapeutically effective amount of the compositions comprised of diclazuril is between about 1/4th and 1/100th but especially about 1/10th of the therapeutically amount of diclazuril that is required for oral administration.

A typical example of the solubilization of diclazuril for use in the compositions contemplated by the invention is to combine about 10 mg of diclazuril with about 20 mg of nicotinamide, about 300 mg of propylene glycol and about 9–10 cc of water. It is contemplated that other solvents can be utilized for preparation of the compositions comprising diclazuril. The skilled artisan can select from among known solvents to fit a particular embodiment, see, e.g. Janssen Pharmaceutica Safety Information for Diclazuril (R-64433) the contents of which is incorporated herein by reference.

In one embodiment of the invention, the effective amount of diclazuril per unit dose for intranasal administration is between about 50 mg and about 1,000 mg, but especially between about 100 mg and about 750 mg. In one embodiment, the effective amount of diclazuril per unit dose is about 350 mg. Depending upon the dosage required for either treatment or prevention of EPM (which can be optimized utilizing methods known in the art), the appropriate amount of diclazuril can thus be solubilized for production of a unit dose or the unit doses can be combined in a multiple treatment vial or container.

Accordingly, therefore, another embodiment of the invention provides a composition adapted for intranasal administration which is comprised of diclazuril, and DMSO in a therapeutically effective amount in which the unit dose is less than the unit dose for a therapeutically amount of diclazuril that is required for oral administration to treat EPM. In preferred embodiments, the therapeutically effective amount of the compositions comprised of diclazuril and DMSO is between about ¼th and ¹⁄₁₀₀th but especially about ¹⁄₁₀th of the therapeutically amount of diclazuril that is required for oral administration One presently preferred embodiment of the invention, comprises a composition adapted for intranasal administration comprising diclazuril solubilized in DMSO. The diclazuril is placed into solution in the DMSO and can be further formulated with other pharmaceutically acceptable carriers and excipients for intranasal administration to fit a particular treatment regimen. A typical unit dosage for administration is between about 50 mg and about 750 mg but is especially between about 100 mg and 500 mg and preferably about 250 mg. In one example, 500 mg of diclazuril is dissolved in 10–15 cc of DMSO and can be utilized for intra nasal administration. This same composition can also be utilized for intravenous administration for treatment of EPM by methods provided for herein.

Typically, the subject equid can be treated via intranasal administration of the solution on a daily basis utilizing, e.g., a catheter and syringe to apply the solution directly to the intranasal mucosa. Depending upon the disposition of the animal, proper restraint should be utilized such as a nose twitch before initiation of the procedure. After proper restraint of the animal, the catheter is advanced up the animal's nostril to the level of the oropharnyx. Most of the solution is injected through the catheter onto the nasal mucosa at the oropharnyx with the remainder being injected as the catheter is slowly withdrawn. For daily administration, as with some of the methods of treatment provided herein, the nostrils may be alternated so as to minimize irritation of the mucosa. The total volume of the composition applied intranasally typically will not exceed 15–20 cc per administration and preferably does not exceed about 10 cc per administration.

Additionally, as set forth in greater detail below, the above solution comprised of diclazuril and DMSO can be further adapted for sustained release of the diclazuril by any of a number of methods known in the art, including the use of excipients and controlled release delivery systems comprised of, e.g., sucrose acetete isobutyrate, methyl cellulose, or microparticles and the like. Frequency of dosing and unit dosage amounts for the sustained compositions set forth herein will vary, of course, depending upon the release characteristics of the delivery system and the specific formulation. However, given the teachings of the invention, optimization of dosage and the therapeutic regimen will be routine to the skilled artisan.

Yet another embodiment of the invention comprises a composition for treatment of EPM adapted for intranasal administration which is comprised of the anti-protozoal nitazoxanide in a therapeutically effective amount in which the unit dose is less than the unit dose required for a therapeutically effective amount of nitazoxanide (as set forth in the references cited above) as would normally be required for the oral administration thereof. In preferred embodiments, the therapeutically effective amount of the compositions comprised of nitazoxanide is between about ¼th and ¹⁄₁₀₀th but especially about ¹⁄₁₀th of the therapeutically effective amount of nitazoxanide that would be required for oral administration.

It can be appreciated that other nitrothiazoles their derivatives, analogs, isomers, salts, and natural metabolites can also be utilized in the compositions for treatment and prevention of EPM disclosed herein.

The dosage of nitazoxanide can vary from between about 100 mg to about 1,500 mg depending upon the specific formulation, but is especially between about 250 mg and about 1000 mg for the intranasal formulations.

Another embodiment of the invention provides a composition adapted for equine intranasal or other parenteral administration which is comprised of pyrimethamine and at least one sulfonamide in a therapeutically effective amount in which the unit dose is less than the unit dose for a therapeutically amount of the same drug combination that is required for oral or other parenteral administration to treat EPM. In preferred embodiments, the therapeutically effective amount of the compositions comprised of pyrimethamine and the sulfonamide is between about ¼th and ¹⁄₁₀₀th but especially about ¹⁄₁₀th of the therapeutically amount of the same drug combination that is required for oral or other parenteral administration. These compositions can, of course, contain more than one sulfonamide in combination with pyrimethamine, as well as additional pharmaceutically acceptable excipients and adjuvants.

Also contemplated are compositions adapted for parenteral (e.g., intramuscular, subcutaneous or intravenous) administration which are comprised of at least one chemical agent one which has anti-protozoal activity, e.g., a triazine based anticoccidial (a triazinedione or a triazinetrione e.g., diclazuril, toltrazuril or sulfonotoltrazuril ) or a nitrothiazole derivative, in a therapeutically effective amount in which the unit dose is less than the unit dose for a therapeutically effective amount of the chemical agent that is required for oral administration to treat or prevent EPM. In preferred embodiments, the therapeutically effective amount of the compositions comprised of the anti-protozoal is between about ½th and ¹⁄₁₀₀th but especially about ¹⁄₁₀th of the therapeutically amount of compound that is required for oral administration.

The invention also provides methods for treating and preventing EPM in an equine, e.g., a horse, which comprise the intranasal administration of a composition such as those provided by the invention. The optimization of the unit dosage amounts and the treatment regimen can be accomplished utilizing methods which are generally known to the skilled artisan.

The invention further provides methods for treating and preventing EPM in an equine, e.g., a horse, which comprise the parenteral, i.e., subcutaneous, intramuscular, intravenous, or transdermal administration of a composition such as those provided by the invention. The optimization of the unit dosage amounts and the treatment regimen can be accomplished utilizing methods which are generally known to the skilled artisan.

In another embodiment of the invention, any of the antiprotozoal agents disclosed herein but especially the triazine-based anticoccidial compounds or the nitrothiazoles including, but not limited to diclazuril, toltrazuril or toltrazuril sulfone, sulfonotoltrazuril and nitazoxanide can be placed in a composition adapted for sustained release. The sustained release composition can comprise any of a number of controlled delivery systems such as microparticles (microspheres or microcapsules), gels, and the like for formulated for injection or absorption. The sustained release compositions of the invention can be administered by any oral or parenteral route including intramuscular, subcutaneous, or intravenous injection. Likewise, the sustained release composition can be adapted for transmucosal or transdermal delivery via a patch, topical application, intranasal or intrauterine delivery and the like.

Materials useful for preparation of the microspheres or microcapsules (microparticles) can include any biocompatable and preferably biodegradable polymer, copolymer or blend. Suitable polymers include polyhydroxyl acids, polyorthoesters, polylactones, polycarbonates, polyphosphazenes, polysaccharides, proteins, polyanhydrides, copolymers thereof and blends thereof. Suitable poly(hydroxy acids) include polyglycolic acid (PGA), polylactic acid (PLA), and copolymers thereof. Preferably the microparticles include poly(D,L-lactic acid) and/or poly(D, L-lactic-co-glycolic acid). Particles with degredation and release times ranging from days to weeks or months can be designed and fabricated, based on factors such as the materials used to prepare the microparticles. Of course, the sustained release compositions contemplated can be utilized in methods of treatment or for prevention of EPM.

The microparticles can be prepared using may method which does not destroy the activity of the active compound. Microparticles can be prepared using single and double emulsion solvent evaporation, spray drying, solvent extraction, solvent evaporation, phase separation, simple and complex coacervation, interfacial polymerization and other methods well known to those of ordinary skill in the art.

Methods developed for making microspheres for drug delivery are described in the literature, for example, as described in Doubrow, M., Ed, Microcapsules and Nano-particles in Medicine and Pharmacy, CRC Press, Boca Raton, 1992. See also, U.S. Pat. Nos. 5,407,609 and 5,654,008 the teachings of which are incorporated herein by reference for methods of making microspheres.

One specific example of a preferred embodiment of a controlled delivery system of the invention is a composition comprised of any of the afore-mentioned therapeutic agents, (including the any of the triazine-based anticoccidials and/or nitazoxanide) and sucrose acetate isobutyrate (SAIB) as set forth is U.S. Pat. No. 5,747,058, the contents of which are incorporated herein by reference. The compositions comprised of an anti-protozaol agent and SAIB, depending upon the formulation, can be administered topically, (e.g., transdermally or transmucosally), subcutaneously or intramuscularily.

Another specific example of a controlled release formulation embodied by the invention is a composition comprised of any of the afore-mentioned therapeutic agents, (including the any of the triazine-based antioccidials and/or nitazoxanide) and methylcellulose (e.g., Methocel). It can be appreciated that other controlled release formulations can be used including other degradable or non-degradable excipients, although degradable excipients are preferred. The compositions comprised of an anti-protozaol agent and Methocel, depending upon the formulation, can be administered topically, (e.g., transdermally or transmucosally), subcutaneously or intramuscularily.

Furthermore, the invention provides the above compositions for use in methods of treating and preventing another common problem of thoroughbred racehorses, a condition called laryngeal hemiplegia, which has an unknown etiology. While not wanted to be limited by theory, it is believed that laryngeal hemiplegia may be caused by or exacerbated by EPM. Laryngeal hemiplegia is a paralysis of the abductor muscles that open the arytenoid cartilages of the throat due to what is believed to be recurrent laryngeal nerve damage. The arytenoid cartilage cannot abduct to open the airway and causes the affected horse to make a "roaring" noise when exercised and he breathes heavily. Therefore, laryngeal hemiplegia, and other potentially EPM-associated diseases and conditions can be treated or prevented by the present invention.

Additional objects, advantages and other novel features of the invention will be set forth in part in the description that follows and in part will become apparent to those skilled in the art upon examination of the foregoing or may be learned with the practice of the invention.

The foregoing description of a preferred embodiment of the invention has s been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A method of treating or preventing a protozoal infection in man or in animals, comprising:

providing a sodium salt of a triazine-based anticoccidial agent, wherein the triazine-based anticoccidial agent is selected from the group consisting of clazuril, diclazuril, letrazuril, toltrazuril, toltrazuril sulfone, sulfonotoltrazuril, and mixtures thereof, and administering to the man or animal a therapeutically effective amount of at least one said sodium salt of a triazine-based anticoccidial agent, wherein said amount is less than about ½ of a therapeutically effective amount of a corresponding non-salt of the triazine-based anticoccidial agent.

2. The method of claim 1, wherein the triazine-based anticoccidial agent is a sodium salt of sulfonotoltrazuril or toltrazuril sulfone.

3. The method of claim 1, wherein the triazine-based anticoccidial agent is a sodium salt of diclazuril.

4. The method of claim 1, wherein the administration is an oral administration.

5. The method of claim 1, wherein the administration is selected from the group consisting of intravenous, intramuscular, subcutaneous, intranasal, transdermal and transmucosal.

6. The method of claim 1, wherein the protozoal infection is selected from the group consisting of sarcosystis, piroplasmosis, babesiosis, toxoplasmosis and cryptosporidiosis.

7. The method of claim 1, wherein the therapeutically effective amount of the triazine-based anticoccidial agent is from between about 0.01 mg/kg and about 20 mg/kg.

8. The method of claim 1, wherein the protozoal infection is equine protozoal myeloencephalitis, the triazine-based anticoccidial agent is diclazuril, the administration is oral and the therapeutically effective amount is between about 0.01 mg/kg and about 20 mg/kg.

9. The method of claim 8, wherein the therapeutically effective amount is from between about 1 mg/kg and about 10 mg/kg.

10. The method of claim 1, wherein the protozoal infection is equine protozoal myeloencephalitis or equine piroplasmosis, the triazine based anticoccidial agent is sulfonotoltrazuril or toltrazuril sulfone, the administration is oral and the therapeutically effective amount is between about 0.01 mg/kg and about 20 mg/kg.

11. The method of claim 10, wherein the therapeutically effective amount is from between about 1 mg/kg and about 10 mg/kg.

12. The method of claim 1, wherein the protozoal infection is equine protozoal myeloencephalitis or equine piroplasmosis, the triazine based anticoccidial agent is diclazuril, the administration is oral and the therapeutically effective amount is between about 0.01 mg/kg and about 20 mg/kg.

13. The method of claim 12, wherein the therapeutically effective amount is from between about 1 mg/kg and about 10 mg/kg.

14. The method of claim 1, wherein the protozoal infection is human cryptosporidiosis in a human subject, the administration is oral and the therapeutically effective amount is from between about 0.01 mg and about 20 mg/kg.

15. The method of claim 14, wherein the therapeutically effective amount is from between about 1 mg/kg and about 10 mg/kg.

16. The method of claim 1, wherein the administration is parenteral.

17. The method of claim 1, wherein the administration is transmucosal.

18. The method of claim 1, wherein the administration is transdermal.

19. The method of claim 1, wherein said amount administered is less than about ⅓ of a therapeutically effective amount of a corresponding non-salt of the triazine-based anticoccidial agent.

20. The method of claim 1, wherein said amount administered is less than about ¼ of a therapeutically effective amount of a corresponding non-salt of the triazine-based anticoccidial agent.

21. The method of claim 1, wherein said amount administered is less than about 1/10 of a therapeutically effective amount of a corresponding non-salt of the triazine-based anticoccidial agent.

* * * * *